United States Patent [19]

Fitzjohn

[11] Patent Number: 5,079,251
[45] Date of Patent: Jan. 7, 1992

[54] NOVEL COMPOUNDS

[75] Inventor: Steven Fitzjohn, Bracknell, United Kingdom

[73] Assignee: Imperial Chemical Industries PLC, London, England

[21] Appl. No.: 551,806

[22] Filed: Jul. 12, 1990

[30] Foreign Application Priority Data

Jul. 12, 1989 [GB] United Kingdom ............... 8915962

[51] Int. Cl.$^5$ ................ A61K 31/495; C07D 241/02; C07D 401/04
[52] U.S. Cl. .................................... 514/255; 514/252; 544/405; 544/406; 544/407; 544/408; 544/409
[58] Field of Search ............... 514/255, 252; 544/405, 544/406, 407, 408, 409

[56] References Cited

U.S. PATENT DOCUMENTS

| 4,293,552 | 10/1981 | Miesel | 544/408 |
| 4,518,599 | 5/1985 | Johnston | 544/408 |
| 4,837,319 | 6/1989 | Yaso et al. | 544/408 |

FOREIGN PATENT DOCUMENTS 062268 4/1982 Japan ................................ 544/408

OTHER PUBLICATIONS

Chemical Abstracts, vol. 107, Abstract No. 7143k.
Ellingson et al., JACS 71, 2798 (1949).
Vekemans et al., Chem. Abst. 99-158384g (1983).
Tutonda et al., Chem. Abst. 106-84557e (1987).

Primary Examiner—Cecilia Shen
Attorney, Agent, or Firm—Cushman, Darby & Cushman

[57] ABSTRACT

Pyrazinone derivatives useful as insecticides have the formula (I):

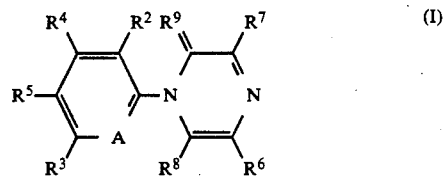

wherein A is N or C-$R^1$; $R^1$ and $R^2$ are independently selected from hydrogen, halogen, haloalkyl, cyano or nitro; $R^3$ and $R^4$ are independently selected from hydrogen, halogen, alkyl or cycloalkyl; $R^5$ is cyano, halo, nitro, alkoxy, haloalkyl, haloalkoxy or —S(O)$_n$R$^{10}$; $R^6$ is halo, cyano, nitro, haloalkyl, haloalkoxy, alkoxycarbonyl or —S(O)$_n$R$^{10}$; $R^7$ is hydrogen, halogen, cyano, nitro, alkyl, alkoxy, alkylthio, haloalkylthio, alkoxycarbonyl, NR$^{11}$R$^{12}$ or haloalkyl; $R^8$ is H, halo, NR$^{11}$R$^{12}$, alkyl, cycloalkyl or S(O)$_n$R$^{10}$; and $R^9$ is oxygen or sulphur; where n is 0, 1 or 2; and $R^{10}$ is alkyl, haloalkyl or cycloalkyl and $R^{11}$ and $R^{12}$ are independently selected from hydrogen, alkyl, cycloalkyl, benzyl or substituted benzyl.

13 Claims, No Drawings

NOVEL COMPOUNDS

The present invention relates to novel pyrazinone derivatives which have insecticidal activity, to processes for their preparation and to their use as insecticides.

According to the present invention there is provided a compound of formula (I):

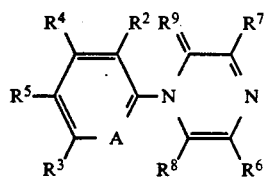

wherein A is N or C-$R^1$; $R^1$ and $R^2$ are independently selected from hydrogen, halogen, haloalkyl, cyano or nitro; $R^3$ and $R^4$ are independently selected from hydrogen, halogen, alkyl or cycloalkyl; $R^5$ is cyano, halo, nitro, alkoxy, haloalkyl, haloalkoxy or -S(O)$_n$$R^{10}$$R^6$ is halo, cyano, nitro, haloalkyl, haloalkoxy, alkoxycarbonyl or S(O)$_n$$R^{10}$$R^7$ is hydrogen, halogen, cyano, nitro, alkyl, alkoxy, alkylthio, haloalkylthio, alkoxycarbonyl, $NR^{11}R^{12}$ or haloalkyl; $R^8$ is H, halo, $NR^{11}R^{12}$, alkyl, cycloalkyl or S(O)$_n$$R^{10}$ and $R^9$ is oxygen or sulphur; where n is 0, 1 or 2; and $R^{10}$ is alkyl, haloalkyl or cycloalkyl and $R^{11}$ and $R^{12}$ are independently selected from hydrogen, alkyl, cycloalkyl, benzyl or substituted benzyl.

Suitable halogen groups for $R^1$, $R^2$, $R^3$, $R^4$, $R^5$, $R^6$, $R^7$ and $R^8$ include fluoro, chloro, bromo or iodo.

The term "alkyl" is used herein includes straight or branched chain alkyl groups, preferably containing up to 6 carbon atoms, for example from 1 to 4 carbon atoms and especially methyl. This applies also to alkyl moieties contained for example in "haloalkyl" and "alkoxy" groups. The term "cycloalkyl" used herein refers to a carbocyclic ring suitably having from 3 to 10 and preferably from 3 to 7 carbon atoms in the ring.

Suitable haloalkyl groups $R^1$, $R^2$, $R^5$, $R^6$ and $R^{10}$ include trihalomethyl groups, in particular trifluoromethyl and pentahaloethyl groups such as pentafluoroethyl.

Suitable substituents for benzyl groups $R^{11}$ or $R^{12}$ include halo such as chloro, fluoro, bromo or iodo, nitro or haloalkyl.

When A is a group C-$R^1$, it is preferable that either $R^1$ or $R^2$ is other than hydrogen. Preferably, both $R^1$ and $R^2$ are other than hydrogen. Suitably $R^1$ and $R^2$ are independently selected from halo (in particular chloro), nitro or cyano.

Suitably $R^3$ and $R^4$ are hydrogen.

A preferred group $R^5$ is a trihalomethyl group in particular trifluoromethyl.

Suitably $R^6$ is hydrogen, halogen (such as bromine or chlorine) trifluoromethyl, pentafluoroethyl, cyano or alkoxycarbonyl (such as methoxycarbonyl). It is especially preferred that $R^6$ is trifluoromethyl or pentafluoroethyl, or that when $R^6$ is cyano, $R^7$ is methyl.

Suitably $R^7$ is hydrogen, halogen such as bromine or chlorine, alkyl (such as methyl) or alkoxycarbonyl (such as methoxycarbonyl).

Suitably $R^8$ is hydrogen.

Suitably $R^9$ is oxygen.

Examples of compounds of formula (I) in which A is C-$R^1$ and $R^3$ and $R^4$ are hydrogen are set out in Table I below.

TABLE I

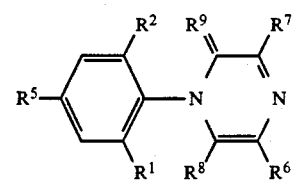

| COMPOUND NO. | $R^1$ | $R^2$ | $R^5$ | $R^6$ | $R^7$ | $R^8$ | $R^9$ |
|---|---|---|---|---|---|---|---|
| 1 | Cl | Cl | CF$_3$ | Br | H | H | O |
| 2 | Cl | NO$_2$ | CF$_3$ | Br | H | H | O |
| 3 | Cl | NO$_2$ | CF$_3$ | H | H | H | O |
| 4 | Cl | Cl | CF$_3$ | CF$_3$ | H | H | O |
| 5 | Cl | NO$_2$ | CF$_3$ | CF$_3$ | H | H | O |
| 6 | Cl | Cl | CF$_3$ | H | H | H | O |
| 7 | Cl | NO$_2$ | CF$_3$ | Br | Br | H | O |
| 8 | Br | CN | CF$_3$ | CF$_3$ | H | H | O |
| 9 | Cl | CN | CF$_3$ | CF$_3$ | H | H | O |
| 10 | Cl | NO$_2$ | CF$_3$ | CN | CH$_3$ | H | O |
| 11 | Cl | NO$_2$ | CF$_3$ | Br | COOCH$_3$ | H | O |
| 12 | Cl | NO$_2$ | CF$_3$ | H | COOCH$_3$ | H | O |
| 13 | Cl | NO$_2$ | CF$_3$ | Cl | COOCH$_3$ | H | O |
| 14 | Cl | NO$_2$ | CF$_3$ | Cl | H | H | O |
| 15 | Cl | Cl | CF$_3$ | Cl | H | H | O |
| 16 | Cl | NO$_2$ | CF$_3$ | COOCH$_3$ | H | H | O |
| 17 | Cl | NO$_2$ | CF$_3$ | CN | H | H | O |

Examples of compounds of formula (I) in which Y is N and $R^3$ and $R^4$ are hydrogen are set out in Table II below.

TABLE II

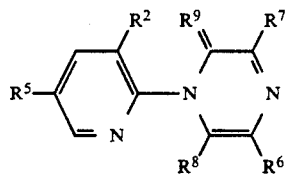

| COMPOUND NO. | $R^2$ | $R^5$ | $R^6$ | $R^7$ | $R^8$ | $R^9$ |
|---|---|---|---|---|---|---|
| 18 | Cl | CF$_3$ | CF$_3$ | H | H | O |

Compounds of formula (I) can be prepared by reacting a compound of formula (II):

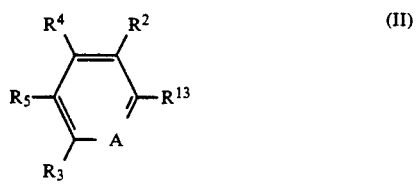

wherein A, $R^2$, $R^3$, $R^4$ and $R^5$ are as defined in relation to formula (I) and $R^{13}$ is a leaving group; with a compound of formula (III):

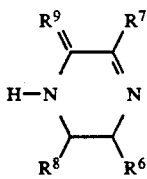
(III)

wherein $R^6$, $R^7$, $R^8$ and $R^9$ are as defined in relation to formula (I) and thereafter if desired converting a group $R^1$-$R^8$ to a different such group.

The reaction is suitably carried out in the presence of a solvent and a base. The base may be for example an alkali metal hydride, an alkali metal alkoxide or an alkali metal carbonate, and the solvent may be a hydrocarbon solvent, such as petroleum ether, an alcohol or an aprotic polar solvent such as dimethylformamide or dimethylacetamide.

Suitable leaving groups $R^{13}$ include halo groups such as fluoro, chloro, bromo or iodo.

If necessary an appropriate catalyst such as a crown ether or copper can be added depending upon the precise nature of $R^{13}$.

Conversion of a group $R^1$-$R^8$ to a different such group may be carried out by conventional methods. In particular compounds of formula (I) wherein $R^1$, $R^2$, $R^5$, $R^6$ and/or $R^7$ is nitro can be converted into the corresponding compound of formula (I) wherein $R^1$, $R^2$, $R^5$, $R^6$ or $R^7$ is halo by reduction of the nitro group to an amino group to form a compound of formula (IV):

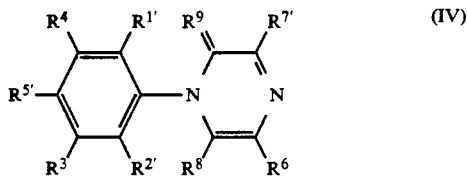
(IV)

wherein $R^3$, $R^4$, and $R^9$ are as defined in relation to formula (I) and $R^{1'}$, $R^{2'}$, $R^{5'}$, $R^{6'}$ and $R^{7'}$ are amino or are equivalent to $R^1$, $R^2$, $R^5$, $R^6$ and $R^7$ as defined in relation to formula (I) respectively provided that at least one of $R^{1'}$, $R^{2'}$, $R^{5'}$, $R^{6'}$ or $R^{7'}$ is amino; and thereafter converting the amino group $R^{1'}$, $R^{2'}$, $R^{5'}$, $R^{6'}$ and/or $R^{7'}$ to halo. Compounds of formula (IV) are novel and as such form a further aspect of the invention.

Reduction of the nitro group to form a compound of formula (IV) can be carried out by reacting the compound with a reducing agent such as stannous chloride in acid conditions, for example, in a solution in concentrated hydrochloric acid. Moderate temperatures of from 2° to 45° C. are suitably employed.

Subsequent halogenation may be carried out by reaction with t-butylnitrite and a copper halide salt such as copper (I) iodide. This step is suitably carried out in an organic solvent such as acetonitrile at low temperatures of from −20° C. to +20° C. preferably at about 0° C.

Further details of the processes for preparation of the compounds may be ascertained from the Examples set out hereinafter.

Certain compounds of formula (II) and (III) are known compounds. For example certain compounds of formula III are described in JACS, 1946, 68, 600; JACS, 1949, 71, 2798; GB Patent No. 928, 152 and U.S. Pat. No. 4,293,552. Others are novel compounds and these form a further aspect of the invention. Compounds of formula II are prepared from known compounds by conventional methods. Compounds of formula (III) can be prepared by diazotisation of a compound of formula (V):

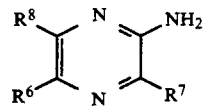
(V)

wherein $R^6$, $R^7$ and $R^8$ are as defined in relation to formula (I).

The diazotisation reaction can be carried out by reacting the compound of formula (V) with a nitrite salt, for example an alkali metal nitrite such as sodium nitrite in the presence of concentrated mixed acids such as concentrated sulphuric acid. The reaction is suitably effected at moderate temperatures for example of from 0° C.–40° C. The resultant diazo intermediate is quenched with water in situ to yield the desired compound of formula (III).

According to a further aspect of the present invention there is provided a compound of formula (III)

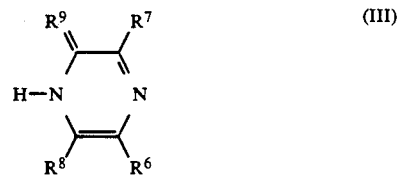
(III)

wherein $R^9$, and $R^8$ are as defined above, $R^6$ is trifluoromethyl, tetraflouoroethyl, bromine, nitro or cyano and $R^7$ is hydrogen or methyl. Preferably $R^6$ is trifluoromethyl and $R^7$ is hydrogen.

Compounds of formula (V) are either known compounds or they can be prepared from known compound by conventional methods.

The compounds of formula (I) may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When dilute to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient (approximately equivalent to from 5–2000 g/ha) is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

a) Pyrethroids such as permethrin, esfenvalerate, deltamethrin, cyhalothrin in particular lambacyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl- (E)-(1R, 3S)-2,2-dimethyl-3-(2-oxothiolan-3-ylidene-methyl)-cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, fensulfothion, fonofos, phorate, phoxim, pyrimiphosmethyl, fenitrothion or diazionon;

c) Carbamates (including aryl carbamates) such as pirimicarb, cloethocarb, carbofuran, ethiofencarb, aldicarb, thiofurox, carbosulfan, beniocarb, fenobucarb, propoxur or oxamyl;

d) Benzoyl ureas such as triflumeron, or chlorofluazuron;

e) Organic tin compounds such as cyhexatin, fenbutatin oxide, aocyclotin;

f) Macrolides such as avermectins or milbemycins, for example, such as avamectin, avermectin, and milbemycin;

g) Hormones such as pheromones;

h) Organochlorine compounds such as benzene hexachloride, DDT, chlordane or dieldrin.

i) Amidines, such as chlordimeform or amitraz.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required.

An example of a rice selective herbicide which can be included in propanil, an example of a plant growth regulator for use in cotton in "Pix", and examples of fungicides for use in rice include blasticides such as blasticidin-S.

The ratio of the compound of the invention to the other active ingredient in the composition will depend upon a number of factors including type of target, effect required from the mixture, etc.

However, in general, the additional active ingredient of the composition will be applied at about the rate as it is usually employed, or at a slightly lower rate if synergism occurs.

The compositions of formula (I) and compositions comprising them have shown themselves active against a variety of insect and other invertebrate pests. They are particularly useful in controlling public health pests such as files and cockroaches. They may also be active against organophosphate and pyrethroid resistant strains of pests such as houseflies (*Musca domestica*). They may be effective in combating both susceptible and resistant strains of the pests in their adult, larval and intermediate stages of growth, and may be applied to the infested host animal by topical, oral or parenteral administration.

The following Preparations and Examples are given by way of illustration.

PREPARATION 1

5-trifluoromethylpyrazin-2-one was prepared as follows.

Sodium nitrite (0.21 g) was added in one batch to concentrated sulphuric acid (2.5 ml) at 2° C. The reaction mixture was then stirred, allowed to warm to room temperature and then heated to 40° C. for 10 minutes. The resulting solution was then cooled to 3° C. and a solution of 2-amino-5-trifluoromethylpyrazine (prepared by the method of Miesel, U.S. Pat. No. 4,293,552, 0.5 g) in concentrated sulphuric acid (3.5 ml) added dropwise. The reaction temperature was not allowed to rise above 5° C. during the addition. After stirring at 5° C. for 10 minutes, the reaction mixture was allowed to warm to room temperature and after 10 minutes heated to 40° C. for 10 minutes. The reaction mixture was then added to ice. Vigorous gas evolution was noted. The mixture was then extracted with ethyl acetate, the organic phase washed with brine, dried with sodium sulphate and evaporated under reduced pressure to give 5-trifluoromethylpyrazine-2-one as a yellow solid.

$^1$H NMR $\delta$ (CDCl$_3$+DMSO) 8.15(1H,s), 7.61(1H,s) (NH signal not observed) $\gamma$(nujol), 3200 (weak), 3075 (moderate), 1660 (strong), 1630 (strong) CM$^{-1}$.

PREPARATION 2

3-Methyl-5-cyanopyrazin-2-one was prepared as follows:

Trifluroacetic anhydride (0.5 ml) was added to a stirred suspension of 3-methyl-5-carbamoylpyrazin-2-one (prepared by the method of Mano, *Chem. Pharm. Bull.*, 1980, 28, 3057; 045 g) in dry 1,4-dioxane (0.5 ml) and dry pyridine (0.48 ml) at a rate that kept the reaction temperature below 5° C. After addition of the trifluoroacetic anhydride was complete the reaction mixture was stirred and allowed to warm to room temperature, and then left to stand at room temperature overnight. The resulting red-brown slurry was diluted with methanol and evaporated to a brown oil. The crude mixture was diluted with ethyl acetate and washed with brine, dilute hydrochloric acid and brine. The organic phase was dried with sodium sulphate and evaporated under reduced pressure to give a brown gum. The gum was treated with petroleum ether (boiling range 60°–80° C.) and cooled in liquid nitrogen to precipitate 3-methyl-5-cyanopyrazin-2-one as a brown solid.

$^1$H NMR $\delta$(CDCl$_3$) 7.55(1H,s); 2.65(bs); 2.45(3H,s).

This material was used without further purification.

PREPARATION 3

3-Methoxycarbonyl-5-bromopyrazin-2-one was prepared as follows:

Concentrated sulphuric acid (5 ml) was stirred and cooled to 2–5° C. and sodium nitrite (0.7 g) added batchwise such that the reaction exotherm did not exceed 10° C. The reaction mixture was allowed to reach room temperature and then warmed to 40° for 2–3 minutes to give a homogeneous solution. The stirred reaction mixture was then cooled to 2°–5° C. and a cooled (2°–5° C.) solution of 2-amino-3-methoxycarbonyl-5-bromopyrazine (JACS, 1949, 71, 2798; 2.32 g) in concentrated sulphuric acid added dropwise so that the reaction temperature did not exceed 5° C. After the addition was complete, the reaction mixture was allowed to warm to 15° C. over three hours and then added dropwise to crushed ice (200 g). The resulting mixture was extracted with ethyl acetate. The organic phase washed with brine, dried with sodium sulphate and evaporated under reduced pressure to give the crude product as a yellow solid. The crude product was used in further experiments without further purification. A portion of the crude product was recrystallised from acetonepetroleum ether (boiling range 60°–80° C.) to give 3-methoxycarbonyl-5-bromopyrazine-2-one as a yellow solid:

Melting point: 118°–120° C.

$^1$H $\delta$(CDCl$_3$): 8.55(1H,s); 4.10(3H,s).

PREPARATION 4

3-Methoxycarbonylpyrazin-2-one was prepared from commercially available 2-amino-3-methoxycarbonylpyrazine by methods analogous to those described in Preparation 3.

$^1$H NMR $\delta$(DMSO-d$_6$) 7.67(1H,d); 7.42(1H,d); 3.76(3H,s).

(NH signal not observed).

PREPARATION 5

3-Methoxycarbonyl-5-chloropyrazin-2-one was prepared from 2-amino-3-methoxycarbonyl-5-chloropyrazine (prepared by the method of Cragoe, J. Med. Chem., 1965, 8, 638) by methods analogous to those described in Preparation 3.

$^1$H NMR $\delta$(CDCl$_3$): 8.47(1H,s); 4.10(3H,s).

PREPARATION 6

5-cyanopyrazin-2-one was prepared as follows:

A stirred suspension of 5-carbamoylpyrazin-2-one (*Chem. Pharm. Bull.*, 1980, 28, 3057; 0.28 g) in dry 1,4-dioxane (5 ml) was cooled to 5° C. prior to adding dry pyridine (0.65 ml). Trifluoroacetic anhydride (0.3 ml) was added dropwise and the reaction mixture allowed to warm to 10° C. After stirring at room temperature for 1 hour the reaction mixture became a slurry and additional trifluoroacetic anhydride (0.25 ml) and pyridine (0.5 ml) was added to give a brown solution. After an additional 1 hour at 10° C. the reaction mixture was added dropwise to methanol and the reaction mixture evaporated under reduced pressure to give a brown gum. The gum was treated with brine and extracted with ethylacetate. The organic phase was washed with dilute hydrochloric acid, brine and dried with sodium sulphate and evaporated under reduce pressure to give an oil that solidified upon scratching to give 5-cyanopyrazin-2-one as a brown solid.

$^1$H MNR $\delta$(DMSO-d$_6$) 8.50(1H,s); 8.15(1H,s); (NH not observed).

This material was used without further purification.

PREPARATION 7

This description illustrates the preparation of 3-amino-5 chloro-4-fluorotrifluoromethylbenzene.

5-Chloro-4-fluoro-3-nitrotrifluoromethylbenzene (50 g) was added to a cooled (5° C.) solution of stannous chloride (140 g) in concentrated aqueous hydrochloric acid (187 ml). After stirring for several hours at the ambient temperature (about 22° C.), the reaction mixture was stood overnight. After basification by the addition of sodium hydroxide, the reaction mixture was extracted with ethyl acetate. The organic layer was washed with water, dried, and the solvent removed by evaporation under reduced pressure. The residual yellow oil was kugelrohr distilled under reduced pressure to give 3-amino-5-chloro-4-fluorotrifluoromethylbenzene (32 g): boiling point 105° C./11 mm Hg;

hu 1H NMR $\delta$(CDCl$_3$) 7.03 (1H, dq), 6.90 (1H, dq), 4.05 (2H, br.s).

PREPARATION 8

This description illustrates the preparation of 3-chloro-4-fluoro-5-cyanotrifluoromethylbenzene.

A solution of 3-amino-5-chloro-4-fluorotrifluoromethylbenzene (3 g) in acetonitrile (10 ml) was added dropwise to a stirred suspension of copper (I) cyanide (1.26 g) in dry acetonitrile (50 ml) whilst the reaction temperature was maintained at 0° C. After the addition was complete, the reaction mixture was allowed to warm to the ambient temperature (about 23° C.) and left overnight. The reaction mixture was poured into water, extracted with diethyl ether, dried over anhydrous magnesium sulphate and filtered. Evaporation of the solvent, under reduced pressure, gave a brown oil, which was flushed through a plug of silica gel using petroleum ether (boiling range 60°-80° C.) containing diethyl ether (20% by volume) as eluent. After removal of the solvent, under reduced pressure, kugelrohr distillation of the residue gave two fractions, the first of which (boiling point 110° C. at 15 mm Hg) was predominantly composed of 3-chloro-4-fluoro-5-cyano trifluorobenzene. This material was used without further purification.

$^1$H NMR $\delta$(CDCl$_3$) 7.95 (1H, m) and 7.85 (1H, m).

PREPARATION 9

This description illustrates the preparation of 4-amino-3-chloro-5-cyanotrifluoromethylbenzene.

Chlorine gas was passed through a stirred solution of 4-amino-3-cyanotrifluoromethyl-benzene (5 g) in carbon tetrachloride (75 ml) until the absence of starting material was confirmed by gas liquid chromatography. Flow of the gas was then stopped and evaporation of the solvent under reduced pressure gave 4-amino-3-chloro-5-cyano-trifluoromethyl benzene as an orange solid (5.5 g).

$^1$H NMR $\delta$(CDCl$_3$/DMSO) 7.67(1H,d), 7.55(1H,d) and 5.85 (2H, br.d).

PREPARATION 10

This description illustrates the preparation of 4-amino-3-bromo-5-cyanotrifluoromethylbenzene. Bromine (a total of 4.9 g) was added in two portions to a stirred suspension of 4-amino-3-cyanobenzotrifluoride (3 g) and sodium acetate trihydrate (1 g) in carbon tetrachloride (65 ml). The mixture was heated to 80° C. until the absence of starting material was confirmed by gas liquid chromatography. Evaporation of the solvent under reduced pressure gave a pale green solid, which was dissolved in ethylacetate, and washed with water and brine. After drying over anhydrous magnesium sulphate, the solvent was removed to give 4-amino-3-bromo-5- cyanotrifluoromethyl benzene (3.63 g) as an oil with solidified on standing.

$^1$H NMR $\delta$(CDCl$_3$) 7.85 (1H,d), 7.65(1H, br.s) and 5.25 (2H,br.s).

PREPARATION 11

This description illustrates the preparation of 3-cyano-4,5-dichlorotrifluoromethylbenzene.

4-Amino-3-chloro-5-cyanotrifluoromethylbenzene (5.1 g) (Preparation 9) in dry acetonitrile (25 ml) was added dropwise to a stirred suspension of copper (II) chloride (3.72 g) and tertiary butyl nitrite (12.24 g) in dry acetonitrile (75 ml) whilst the temperature was maintained between 0° and +5° C. After the addition was complete, stirring was continued for a further 2 hours, whereupon the reaction mixture was diluted with dilute aqueous hydrochloric acid, and extracted with ethylacetate. The organic layer was washed with water, and after drying over anhydrous magnesium sulphate, evaporation of the solvent under reduced pressure gave an orange oil which crystallised on standing. Kugelrohr distillation gave 3-cyano-4,5-dichloro-trifluoromethylbenzene as a pale yellow solid which crystallised on standing.

$^1$H NMR $\delta$(CDCl$_3$) 7.95(1H,d) and 7.85(1H,d).

PREPARATION 12

4-Amino-3-bromo-5-cyanotrifluoromethylbenzene (Preparation 10) was converted into 3-bromo-4-chloro-5-cyanotrifluoromethylbenzene using the general method of preparation 11.

$^1$H NMR $\delta$(CDCl$_3$) 8.12 (1H,d) and 7.90(1H,d).

PREPARATION 13

This description illustrates an alternate preparation of 3-chloro-4-fluoro-5-cyano-trifluoromethylbenzene.

Dry potassium fluoride (1.94 g) was added to a flask containing dry toluene (31 ml), dry dimethylformamide (7.8 ml) and a catalytic amount of 18-crown-6. The stirred mixture was heated to reflux, and approximately 25 mls of the distillate was collected. After cooling to ambient temperature, 3-cyano-4,5-dichlorobenzotrifluoromethylbenzene (4 g) was added in one portion, and the stirred mixture was heated to 130° C. for 16 hours, and then to 145° C. for 24 hours. After cooling to ambient temperature, the reaction mixture was filtered, the residue washed with ethylacetate, and the combined filtrate washed with brine. After drying over anhydrous magnesium sulphate, evaporation under reduced pressure gave a brown oil which was subjected to kugelrohr distillation, to give 3-chloro-4-fluoro-5-cyanotrifluoromethylbenzene as a pale yellow liquid (3.17 g).
$^1$H NMR δ(CDCl$_3$) 7.95(1H,dq) and 7.85(1H,dq).

PREPARATION 14

3-Bromo-4-fluoro-5-cyanotrifluoromethylbenzene was prepared from 3-bromo-4-chloro-5-cyanotrifluromethylbenzene (Preparation 12) using the general method of Preparation 13.
$^1$H NMR δ(CDCl$_3$) 8.10(1H, dq) and 7.89(1H,dq).

PREPARATION 15

This description illustrates an alternative procedure from that described in Preparation 11 for the preparation of 3-cyano-4,5-dichlorotrifluroromethylbenzene.

Sodium nitrite (2.3 g) was added in portions to concentrated sulphuric acid (18.0 g) at room temperature. 3-Amino-4,5-dichlorotrifluoromethylbenzene (6.9 g) was added portionwise, during the course of which time acetic acid (15 ml) was added to the stirred slurry. This slurry was then added dropwise to a cooled (9°-10° C.) solution of sodium cyanide (5.9), copper (I) cyanide (5.4 g), and sodium acetate trihydrate (60 g) in water (60 ml).

After the addition was complete, the mixture was stirred and allowed to warm to ambient temperature over the course of one hour, and then stirred for a further hour. The pH of the reaction mixture was adjusted to 8.5 using aqueous sodium hydroxide solution and the mixture was then extracted with ethylacetate. The organic layer was washed with water and brine and dried over anhydrous magnesium sulphate. Evaporation of the solvent under reduced pressure and distillation gave 3-cyano-4,5-dichlorotrifluoromethylbenzene characterised by its NMR spectrum as in preparation 11.

EXAMPLE 1

This Example illustrates the preparation of 1-(2,6-dichloro-4-trifluoromethylphenyl)-5-trifluoromethylpyrazin-2-one (Compound No. 4 in Table I).

A dry reaction flask was purged with nitrogen and charged with a 50% suspension of sodium hydride (0.060 g). The sodium hydride was washed with petroleum ether (fraction 40°-60° C.) and suspended in dry dimethylformamide (DMF, 5 ml). The stirred mixture was cooled to 8°-10° C. prior to the addition of 5-trifluoromethylpyrazin-2-one (0.2 g; Preparation 1) portionwise; when the addition was complete the reaction was stirred at 8°-10° C. for an additional 25 minutes. 3,5-Dichloro-4-fluoro-trifluoromethylbenzene (0.570 g) was added and the reaction mixture allowed to reach room temperature. The reaction mixture was heated to 55°-60° C. for 30 hours.

The reaction mixture was allowed to cool, diluted with water and extracted with ethyl acetate. The organic phase was washed with brine, dried with sodium sulphate and evaporated under reduced pressure to give an oily residue. The crude reaction product was subjected to column chromatography using silica gel and diethylether (10% by volume) in petroleum ether (boiling range 40°-60° C.) as eluant, to give 1-(2,6-dichloro-4-trifluoromethylphenyl)-5-trifluoromethylpyrazin-2-one as a white solid:

·Melting point: 109°-111° C.; $^1$H NMR δ(CDCl$_3$) 8.38(1H,s); 7.81(2H,s); 7.42(1H,s).

EXAMPLE 2

The following compounds were prepared by methods analogous to those described in Example 1.
(i) Compound No 1 in Table I:
  Melting point: 155°-159° C.; $^1$H NMR δ(CDCl$_3$) : 8.20(1H,s); 7.80(2H,s); 7.10(1H,s).
(ii) Compound No 6 in Table I:
  Melting point: 115°-117° C.; $^1$H NMR δ(CDCl$_3$) 8.36(1H,d J 2Hz); 7.80(2H,s); 7.49 (1Hd J 8Hz); 6.90(1H,m).
(iii) Compound No 15 in Table I:
  Melting point: 183°-185° C.; $^1$H NMR δ(CDCl$_3$) : 8.19(1H,s); 7.80(2H,s); 7.03(1H,s).

EXAMPLE 3

This Example illustrates the preparation of 1-(2-nitro-4-trifluoromethyl-6-chlorophenyl)-5-trifluoromethylpyrazin-2-one. (Compound No 5 in Table I).

A dry reaction flask was purged with nitrogen and charged with a 50% suspension of sodium hydride (0.11 g). The sodium hydride was washed with petroleum ether (fraction 40°-60° C.) and suspended in dry dimethylformamide (DMF, 10 ml). The stirred reaction mixture was cooled to 35 7°-10° C., prior to the addition of 5-trifluoromethylpyrazin-2-one (0.4 g) portionwise; when the addition was complete the reaction was stirred at 7°-10° C. for an additional 15 minutes. 3-Nitro-4-fluoro-5-chloro-trifluoromethylbenzene (1.170 g) was added dropwise keeping the reaction temperature below 10° C. After stirring at 5°-10° C. for 4 hours the reaction mixture was stirred at room temperature for 18 hours.

The reaction mixture was diluted with water and extracted with ethyl acetate. The organic phase was washed with brine, dried with sodium sulphate and evaporated under reduced pressure to give the crude reaction product. Chromatography using silica gel and diethyl ether (20% by volume) in petroleum ether, gave yellow solid. This solid was triturated with diethylether (20% by volume in petroleum ether), collected by filtration, washed on the pad with petroleum ether and dried to give 1-(2-nitro-4-trifluoromethyl-6-chlorophenyl)-5-trifluoromethylpyrazin-2-one as a yellow solid.
  Melting point: 145°-147° C.; $^1$H NMR δ(CDCl$_3$) 8.43(1H,d J 2Hz); 8.35(1H,s); 8.21 (1H,d J 2Hz); 7.52(1H,s).

EXAMPLE 4

The following compounds were prepared by methods analogous to those described in Example 3.
(i) Compound No 2 in Table I:
  Melting point: 135°-138° C.; $^1$H NMR δ(CDCl$_3$) 8.40(1H,d J 2Hz); 8.19(1H,d J 2Hz); 8.15(1H,s); 7.20(1H,s).
(ii) Compound No 3 in Table I:
  Melting point: 173°-175° C. $^1$H NMR δ(CDCl$_3$) : 8.37(1H,s); 8.30(1H,s); 8.18(1H,s); 7.53(1H,d J 8Hz).
(iii) Compound No 7 in Table I:
  Melting point: 149°-151° C. $^1$H NMR δ(CDCl$_3$): 8.42(1H,s); 8.20(1H,s); 7.25(1H,s).

EXAMPLE 5

This Example illustrates the preparation of 1-(2-cyano-4-trifluoromethyl-6-bromophenyl)-5-trifluoromethylpyrazin-2-one (Compound No 8 in Table I).

A dry reaction flask was purged with nitrogen and charged with a 50% suspension of sodium hydride (0.032 g). The sodium hydride was suspended in dry dimethylformamide (DMF, 2 ml). To the stirred reaction mixture was added 5-trifluoromethylpyrazin-2-one (0.104 g) portionwise; when the addition was complete the reaction was stirred at room temperature for 45 minutes. 3-Cyano-4-fluoro-5-bromotrifluoromethylbenzene (0.33 g; Preparation 14) was added and the resulting brown reaction mixture was stirred at room temperature for 4 hours.

The reaction mixture was diluted with water and extracted with ethyl acetate. The organic phase was washed with brine, dried with sodium sulphate and evaporated under reduced pressure to give the crude reaction product as a brown oil. Chromatography using silica gel and ethyl acetate (30% by volume) in hexane as eluant gave the desired product as a pale yellow solid.

Melting point 117°–118° C. $^1$H NMR $\delta$(CDCl$_3$): 8.41(1H,m); 8.30(1H,m); 8.09 (1H,m); 7.48(1H,m).

EXAMPLE 6

The following compound was prepared using the general method of Example 5. 1-(2-cyano-4-trifluoromethyl-6-chlorophenyl)-5-trifluoromethylpyrazin-2-one (Compound No 9 in Table I). In this preparation, the reaction mixture was stirred at room temperature overnight after the addition of the 3-Cyano-4-fluoro-5-chloro-trifluoromethylbenzene (Preparation 13).

Melting point 133°–135° C. $^1$H NMR $\delta$(CDCl$_3$): 8.41(1H,m); 8.16(1H,m); 8.07 (1H,m); 7.50(1H,m).

EXAMPLE 7

The following compounds were prepared using the general method of Example 3, but with the indicated variations in reaction temperature/time profile: 1-(2-nitro-4-trifluoromethyl-6-chlorophenyl)-5-cyanopyrazin-2-one (Compound No 10 in Table I): The reaction product of 3-methyl-5-cyanoprazin-2-one (Preparation 2) and sodium hydride in dimethylformamide was stirred at −10° to −5° C. for 30 minutes before the addition of 3-nitro-4-fluoro-5-chloro-trifluoromethyl benzene in one portion, and the reaction mixture was thereafter allowed to warm from −10° C. to room temperature and stirred overnight.

Melting point 130°–134° C. $^1$H NMR $\delta$(CDCl$_3$): 8.43(1H,m); 8.20(1H,m); 7.51 (1H,s); 2.55(3H,s).

1-(2-nitro-4-trifluoromethyl-6-chlorophenyl)-3-methoxycarbonyl-5-bromopyrazin-2-one (Compound No 11 in Table I): The reaction product of 3-methoxycarbonyl-5-bromoprazin-2-one (Preparation 3) and sodium hydride in dimethylformamide was stirred at −8° C. for 15 minutes before the addition of 3-nitro-4-fluoro-5-chlorotrifluoromethylbenzene in one portion, and the reaction mixture was thereafter allowed to warm to 15° C. over a period of 90 minutes and then to room temperature before finally being stirred at room temperature for 18 hours.

Melting point 177°–179° C. $^1$H NMR $\delta$(CDCl$_3$): 8.43(1H,s); 8.19(1H,s); 7.46 (1H,s); 3.98(3H,s).

1-(2-nitro-4-trifluoromethyl-6-chlorophenyl)-3-methoxycarbonylpyrazin-2-one (Compound No 12 in Table I): The reaction product of 3-methoxycarbonyl-prazin-2-one (Preparation 4) and sodium hydride in dimethylformamide was stirred at −5° to −2° C. for 30 minutes before the addition of 3-nitro-4-fluoro-5-chlorotrifluoromethylbenzene, and the reaction mixture was thereafter stirred at −2° to 0° C. for 1 hour prior to allowing the reaction to warm to room temperature when it was stirred overnight.

Melting point 143°–145° C. $^1$H NMR $\delta$(CDCl$_3$): 8.42(1H,d); 8.18(1H,d); 7.67 (1H,d); 7.25(1H,d); 3.99(3H,s).

1-(2-nitro-4-trifluoromethyl-6-chlorophenyl)-3-methoxycarbonyl-5-chloropyrazin-2-one (Compound No 13 in Table I): The reaction product of 3-methoxycarbonyl-5-chloroprazin-2-one (Preparation 5; added in four portions over a period of 5 minutes) and sodium hydride in dimethylformamide was stirred at −8° C. for 5 minutes before the addition of 3-nitro-4-fluoro-5-chloro-trifluoromethylbenzene. This caused the precipitation of an orange solid and the reaction mixture was allowed to warm slowly to 10° C. give a homogeneous solution. The mixture was then cooled to 5° C. and stirred at that temperature for 1 hour before being allowed to warm to room temperature and stirred overnight.

Melting point 154°–155° C. $^1$H NMR $\delta$(CDCl$_3$): 8.43(1H,d); 8.19(1H,d); 7.36 (1H,s); 3.99(3H,s).

1-(2-nitro-4-trifluoromethyl-6-chlorophenyl)-5-chloropyrazin-2-one (Compound No 14 in Table I): The reaction product of 5-chloroprazin-2-one (Journal of Organic Chemistry, 1964, 29, 2491) and sodium hydride in dimethylformamide was stirred at 5° to 10° C. for 30 minutes before the addition of 3-nitro-4-fluoro-5-chlorotrifluoromethyl benzene in one portion, and the reaction mixture was thereafter stirred at that temperature for 2 hours before being allowed to warm to room temperature and stirred overnight.

Melting point 142°–143° C. $^1$H NMR $\delta$(CDCl$_3$): 8.39(1H,d); 8.17(1H,d); 8.15 (1H,s); 7.14(1H,s).

1-(2-nitro-4-trifluoromethyl-6-chlorophenyl)-5-methoxypyrazin-2-one (Compound No 16 in Table I): The reaction product of 5-methoxyprazin-2-one (Chem. Pharm. Bull., 1980, 28, 3057) and sodium hydride in dimethylformamide was stirred at −10° C. for 30 minutes before the addition of 3-nitro-4-fluoro-5-chlorotrifluoromethyl benzene, and the reaction mixture was thereafter allowed to warm to room temperature and stirred overnight.

Melting point 172°–173° C. $^1$H NMR $\delta$(CDCl$_3$): 8.43(1H,d); 8.33(1H,s); 8.20 (1H,s); 3.98(3H,s).

1-(2-nitro-4-trifluoromethyl-6-chlorophenyl)-5-cyanopyrazin-2-one (Compound No 17 in Table I): The reaction product of 5-cyanoprazin-2-one (Preparation 6) and sodium hydride in dimethylformamide (a suspension) was stirred at −10° C. for 5 minutes before the addition of 3-nitro-4-fluoro-5-chloro-trifluoromethylbenzene in one portion, and the reaction mixture was thereafter stirred vigorously and allowed to warm to room temperature. The reaction mixture was then stirred at room temperature for 60 hours.

Melting point 126°–128° C. $^1$H NMR $\delta$(DMSO-d$_6$) 9.30(1H,s); 9.01(1H,d); 8.89 (1H,d); 8.60 (1H,s). 1-(3-chloro-5-trifluoromethylpyridin-2-yl)-5-trifluoromethylpyrazin-2-one (Compound No 18 in Table I): The reaction product of 5-trifluoromethylpyrazin-2-one and sodium hydride in dimethylformamide was stirred for 30 minutes at room temperature before the addition of 2-fluoro-3-chloro-5-trifluoromethylpyridine, and the reaction mixture was thereafter stirred overnight at room temperature.

Melting point 96°–97° C. $^1$H NMR $\delta$(CDCl$_3$): 8.83(1H,m); 8.32(1H,s); 8.22 (1H,m); 7.77 (1H,s).

The activity of the compounds of formula (I) was determined using a variety of the pests. The compound was used in the form of liquid preparations containing 500 parts per million (ppm) by weight of the compound. The preparations were made by dissolving the compound in acetone and diluting the solutions with water containing 0.01% by weight of a wetting agent sold under the trade name "SYNPERIONIC" NX until the liquid preparations contained the required concentration of the Product. "SYNPERIONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

The results of the tests are given in Table III for each of the Products, at the rate in parts per million given in the second column as a grading of mortality designated as A, B or C wherein A indicates 80-100% mortality, B indicates 50-79% mortality and C indicates less than 50% mortality.

In Table IV the pest organism used is designated by a letter code and the pest species, the support medium or food, and the type and duration of test is given.

TABLE III

| Compound No | Rate (ppm) | MP | NC | MD | BG | SP | DB |
|---|---|---|---|---|---|---|---|
| 1 | 500 | B | C | C | C | C | C |
| 2 | 500 | C | C | C | C | A | B |
| 3 | 500 | C | B | C | C | A | C |
| 4 | 500 | C | B | A | A | A | A |
| 5 | 500 | C | C | A | A | C | B |
| 6 | 500 | C | C | C | C | C | B |
| 7 | 500 | C | C | C | C | C | C |
| 8 | 500 | C | C | A | A | C | C |
| 9 | 500 | C | C | B | A | — | A |
| 10 | 500 | C | A | B | C | A | C |
| 11 | 500 | C | C | C | C | A | C |
| 12 | 500 | C | C | C | C | C | C |
| 13 | 500 | C | C | C | C | B | C |
| 14 | 500 | C | C | C | C | C | C |
| 15 | 500 | C | B | C | C | C | C |
| 16 | 500 | C | C | C | C | B | A |
| 17 | 500 | C | C | C | C | B | C |
| 18 | 500 | C | B | A | C | A | A |

TABLE IV

| Code Letters | Test Species | Support medium/food | Type of test | Duration (days) |
|---|---|---|---|---|
| MP | Myzus persicae (aphids) | French bean leaf | Contact | 3 |
| NC | Nephotettix cincticeps (green leafhopper - nymphs) | Rice plant | Contact | 2 |
| MD | Musca domestica (houseflies - adults) | Cotton wool/ sugar | Contact | 3 |
| BG | Blattella germanica (Cockroach nymphs) | Plastic Pot | Residual | 3 |
| SP | Spodoptera exigua (lesser army worm - larvae) | Cotton leaf | Residual | 2 |
| DB | Diabrotica balteata (rootworm - larvae) | Filter paper/ maize seed | Residual | 2 |

"Contact" indicates a test in which both the medium and the pests were treated.
"Residual" indicates a test in which the medium was treated prior to infestation

What is claimed is:

1. A compound of formula (I):

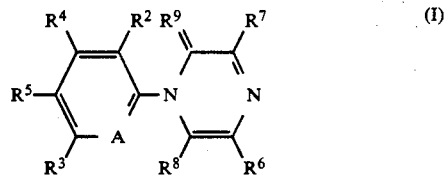

wherein A is N or C-R$^1$; R$^1$ and R$^2$ are independently selected from hydrogen, halogen, halo-lower alkyl, cyano or nitro; R$^3$ and R$^4$ are independently selected from hydrogen, halogen, lower alkyl or cycloalkyl; R$^5$ is cyano, halo, nitro, alkoxy, halo-lower alkyl, halo-lower alkoxy or -S(O)$_n$R$^{10}$; R$^6$ is halo, cyano, nitro, halo-lower alkyl, halo-lower alkoxy, lower alkoxycarbonyl or -S(O)$_n$R$^{10}$; R$^7$ is hydrogen, halogen, cyano, nitro, lower alkyl, lower alkoxy, lower alkylthio, halo-lower alkylthio, lower alkoxycarbonyl, NR$^{11}$R$^{12}$ or halo-lower alkyl; R$^8$ is H, halo, NR$^{11}$R$^{12}$, lower alkyl, cycloalkyl or S(O)$_n$R$^{10}$; and R$^9$ is oxygen or sulphur; where n is 0, 1 or 2; and R$^{10}$ is lower alkyl, halo-lower alkyl or cycloalkyl and R$^{11}$ and R$^{12}$ are independently selected from hydrogen, alkyl, cycloalkyl, benzyl or benzyl substituted with halogen, nitro or halo-lower alkyl.

2. A compound according to claim 1 wherein A is -C-R$^1$ and at least one of R$^1$ and R$^2$ is other than hydrogen.

3. A compound according to claim 2 wherein R$^1$ and R$^2$ are independently selected from halo, nitro and cyano.

4. A compound according to any of the preceding claims wherein R$^3$ and R$^4$ are both hydrogen.

5. A compound according to any of the preceding claims wherein R$^5$ is trifluoromethyl.

6. A compound according to any of the preceding claims wherein R$^6$ is hydrogen, halogen, trifluoromethyl, pentafluoroethyl, cyano or alkoxycarbonyl.

7. A compound according to claim 6 wherein R$^6$ is cyano and R$^7$ is methyl.

8. A compound according to any of claims 1 to 6 wherein R$^7$ is hydrogen, halogen, alkyl or alkoxycarbonyl.

9. A compound according to any of the preceding claims wherein R$^8$ is hydrogen.

10. A compound according to any of the preceding claims wherein R$^9$ is oxygen.

11. A compound of formula (III):

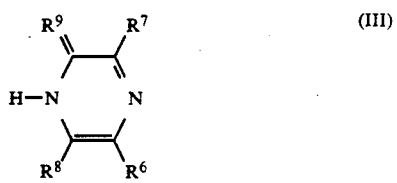

wherein R$^9$, and R$^8$ are as defined in relation to formula (I) in claim 1, R$^6$ is trifluoromethyl, tetraflouoroethyl, bromine, nitro or cyano and R$^7$ is hydrogen or methyl.

12. A method of killing or controlling insect or acarine pests which method comprises applying to the pest or to a locus thereof on effective amount of a compound of formula (I) as defined in claim 1.

13. An insecticidal or acaricidal composition comprising an insecticidally or acaricidally effective amount of a compound of formula (I) in combination with a diluent or carrier.

* * * * *